United States Patent [19]

Inui

[11] Patent Number: 5,185,357

[45] Date of Patent: Feb. 9, 1993

[54] INDUSTRIAL ANTIFUNGAL COMPOSITION

[75] Inventor: Keiichiro Inui, Matsubara, Japan

[73] Assignee: Shinto Paint Co., Ltd., Amagasaki, Japan

[21] Appl. No.: 657,788

[22] Filed: Feb. 21, 1991

[30] Foreign Application Priority Data

Feb. 26, 1990 [JP] Japan ................... 2-46672

[51] Int. Cl.$^5$ ............... A01N 43/52; A01N 43/80
[52] U.S. Cl. ........................ 514/372; 514/388
[58] Field of Search ................ 514/372, 388

[56] References Cited

U.S. PATENT DOCUMENTS 4,105,431 8/1978 Lewis et al. ................... 71/67

OTHER PUBLICATIONS

Worthing et al., The Pesticide Manual, 8th ed. (1987) pp. 127–128.

Primary Examiner—Allen J. Robinson
Attorney, Agent, or Firm—Wenderoth, Lind & Ponack

[57] ABSTRACT

An antifungal composition made up of at least one compound represented by the formula (I):

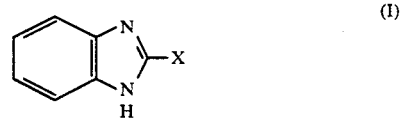

wherein X represents a group of the formula —NH-COOR in which R is —$CH_3$ or —$C_2H_5$, or 4-thiazolyl group and at least one compound represented by the formula (II):

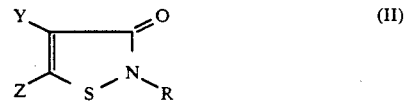

wherein Y represents hydrogen or halogen, Z represents halogen and R represents alkyl group of 1 to 8 carbon atoms. The composition preferably comprises 10 to 90% by weight of the compound(s) of formula (I).

1 Claim, No Drawings

INDUSTRIAL ANTIFUNGAL COMPOSITION

This invention relates to an industrial antifungal composition, more particularly to an industrial antifungal composition having an excellent antifungal activity and which is excellent in safety.

Heretofore, halogenated phenol compounds or organotin compounds have frequently been used as active ingredients of industrial antifungal agents. However, these compounds have high acute toxicity as well as chronic toxicity and are relatively hard to be decomposed. Therefore there is an ever-present fear for a secondary environmental pollution caused by accumulation of said compounds in the antifungal agents containing the same, so that these compounds have now come to be unsuitable for use as active ingredients in the industrial antifungal agents.

In these circumstances antifungal agents which are higher in safety have come to be developed enthusiastically. For example, there have been developed such compounds as 2-benzimidazole carbamic acid esters, 2-(4-thiazolyl)benzimidazole, etc. However, as revealed from MIC(minimum inhibition concentrations) of these benzimidazole compounds against various species of fungi, they are not useful as active ingredients of fungicides to be applied to industrial materials and products which are usually exposed to risk of contamination with a wide variety of species of fungi, although these compounds are useful when used as fungicidal agents for agricultural and horticultural application wherein the contamination of plants with relatively limited species of fungi becomes a problem. For this reason, there has been made an attempt to broaden the fungicidal spectrum or increase fungi resistance of antifungal agents by combining a plurality of antifungal agents different in kind. However, the fact is that the effect as obtained thereby is usually limited only to that of one of the antifungal agents or is merely of the expected addition of the effects respectively of such antifungal agents, at most.

The present invention is to solve such problems associated with the above mentioned prior technology. Thus an object of the present invention is to provide an industrial antifungal composition which has an excellent antifungal activity as well as excellent broad spectrum against a wide variety of species of fungi and, moreover, which is excellent in safety and free from tendency to accumulation and therefore is useful and effective even with a very small amount.

I have conducted extensive researches with a view of solving such problems as mentioned above and have accomplished the present invention on the basis of the finding that a composition comprising a combination of a particular compound represented by the formula (I) and a particular compound represented by the formula (II), both to be mentioned later, has a remarkable increased antifungal activity as compared with the case where each of these compounds is used singly.

Briefly, the present invention provides an industrial antifungal composition which comprises, as the active ingredients, at least one compound represented by the general formula (I):

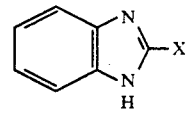

wherein X represents a group of the formula —NHCOOR in which R is —CH$_3$ or —C$_2$H$_5$, or 4-thiazolyl group and at least one compound represented by the general formula (II):

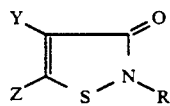

wherein Y represents hydrogen or halogen, Z represents halogen and R represents alkyl group of 1 to 8 carbon atoms.

The industrial antifungal composition of the present invention contains as its active ingredients both the compound of the formula (I) and the compound of the formula (II). Thus these compounds must be used in combination, thereby the antifungal activity of the composition is sharply increased and, consequently, the composition comes to have excellent antifungal activities against a wide variety of species of fungi, and comes to be high in safety and free from tendency to accumulation and therefore comes to be useful or effective even with the use in a minimum amount.

Examples of the compounds of the formula (I) to be used in the industrial antifungal compositions of the present invention include methyl 2-benzimidazole carbamate, ethyl 2-benzimidazole carbamate, 2-(4-thiazolyl)benzimidazole, etc. In this connection, these benzimidazole compounds are known to be high in safety and free from tendency to accumulation. As mentioned previously, however, they have selectivity to fungicidal spectrum and are of no practical use when they are used singly.

The compounds of the formula (II) to be used in the industrial antifungal compositions of the present invention includes, for example, 4,5-dichloro-2-methyl isothiazoline 3-one, 5-chloro-2-methyl isothiazoline 3-one, 4,5-dichloro-2-octyl isothiazoline 3-one, etc. These isothiazoline compounds are free from tendency to accumulation and the necessary amount of use may be minimized owing to excellent synergistic effect obtained by the use of the aforementioned imidazole compounds in combination therewith, and thus in accordance with the present invention it is possible to provide an industrial antifungal composition which is substantially harmless.

The proportion of the compounds of the formula (I) to the compounds of the formula (II) to be used in the industrial antifungal composition of the present invention may be varied over a wide range. However the benzimidazole compound of the formula (I) is used preferably in an amount of 10–90% by weight, more preferably 10–50% by weight, based on the total weight of the benzimidazole compounds of the formula (I) and the isothiazoline compounds of the formula (II) to be used in the antifungal composition, because the synergistic effect of these two compounds is markedly exhibited in particular.

According to the particular purpose for which they are used, the antifungal composition of the present invention may be applied, as they are, directly to the objects to which they are applied, or they may be applied thereto after having been formed into such various formulations, for example, as oil type formulations prepared by dissolving the present compositions in such liquids as alcohols, glycols, alkyl ethers of glycol and aromatics; emulsion type formulation prepared by adding to said oil type formulations, nonionic surfactants, such as polyoxyethylene alkyl ethers, polyoxyethylene alkylaryl ether, polyoxyethylene alkyl esters, sorbitan fatty acid esters, polyoxyethylene sorbitan fatty acid esters, etc. and anionic surfactants, such as sulfate ester salts of polyethylene glycol ether, sulfonates of fatty acid ester, phosphates ester salts of polyethylene glycol ether, etc.; aqueous suspensions (flowable formulations) prepared by rendering the present antifungal compositions hydrophilic on the surface thereof in water with nonionic surfactants, such as polyoxyethylene alkylphenyl ethers, polyoxyethylene alkyl ethers, polyoxyethylene styrylphenyl ethers, etc.; dispersing the thus treated compositions with anionic surfactants, such as dialkyl sulfosuccinates, condensates of naphthalenesulfonic acid with formalin, polyoxyethylene alkylallylethers, etc., and adding to the thus dispersed compositions such protective colloids as guar gum, gum arabic, tragacanth gum, xanthan gum, alkali salts of carboxymethyl cellulose, ammonium arginate, polyvinyl alcohol, polyvinyl pyrrolidone, sodium polyacrylate, polyacrylic acid amide, etc., and thickeners; fine particulate formulations prepared by mixing the present compositions with clay, talc, calcium carbonate, amorphous silicon dioxide, aluminum silicate, etc., wettable powders prepared by adding to said fine particulate formulations such nonionic surfactants as polyoxyethylene alkyl ethers, polyoxyethylene alkylaryl ethers, polyoxyethylene alkylesters, sorbitan fatty acid esters, and such anionic surfactants as sulfate ester salts of polyethylene glycol ether, sulfonates of fatty acid esters, phosphate ester salts of polyethylene glycol ether; and other granular and paste formulations.

Furthermore, the antifungal compositions of the present invention can also be used in admixture with other known antifungal compounds such as N-fluorodichloromethylthio phthalimide, o-phenylphenyl, bis(-tributyltin)oxide, 2-(thiocyanomethylthio) benzothiazole, N,N-dimethyl-N'-phenyl(N'-fluorodichloromethylthio)-phthalimide, A1-N-nitroso-N-cyclohexyl hydroxylamine, Zn-2-pyridinethiol-1-oxide, 2,4,5,6-tetrachloroisophthalonitrile, diiodomethyl-p-torylsulfone, 2,4,4'-trichloro-2'-hydroxydiphenyl ether, etc.; bacteriocides such as 1,2-benzisothiazoline-3-one, methylene bisthiocyanate, tetrahydro-3,5-dimethyl-2H-1,3,5-thiadiazine-2-thione, bisbromoacetoxyethane, 2-bromo-2-nitrobutane-1,3-diol, 2-bromo-2-bromomethyl-glutaronitrile, 2,2-dibromo-3-nitrilopropionamide, bis(-tribromomethyl) sulfone, etc.; and insecticides such as 0,0-dimethyl-0-(3-methyl-1,4-nitrophenyl) phosphorothioate (Fenitrothion), 0,0-dimethyl-0-(3-methyl-4-methylthiophenyl) phosphorothioate(Fenthion), 0-(2,2-dichlorovinyl)-0,0-dimethyl phosphate(Dichlorvos), 0,0-diethyl-0-(2-isopropyl-4-methyl-6-pyrimidinyl) phosphorothioate(Diazinon), 0-2,4-dichlorophenyl-0-ethyl-s-propyl phosphorodithoate(Prothiofos), (E)-0-2-isopropoxycarbonyl-1-methylvinyl-0-methyl-N-ethyl phosphoramidothioate(Propetamphos), 0,0-dimethyl-0-(3,5,6-trichloro-2-pyridyl)-phosphorothioate(Chlorpyrifos-methyl), etc.

The antifungal compositions of the present invention are applicable to various industrial materials and products, for example, paints, coating colors, adhesives, fibers, wood and bamboo products, leather products, paper products, electronic parts, wall decorative materials, resin molded articles, etc.

This invention will be explained concretely by the following examples and test examples, which are given by way of illustration but not for limitation of the scope of the invention. In these examples, percentages and parts are by weight unless specified otherwise, and names of the compounds used therein are abbreviated as in the following.

| Compounds of the general formula (I) | |
|---|---|
| Methyl 2-benzimidazole carbamate: | BICM |
| Ethyl 2-benzimidazole carbamate: | BICE |
| 2-(4-Thiazolyl)benzimidazole: | TBZ |
| Compounds of the general formula (II) | |
| 4-chloro-2-methyl isothiazoline 3-one: | CMIT |
| 4,5-dichloro-2-octhyl isothiazoline 3-one: | DOIT |
| Other known antifungal compounds | |
| 2,4,6-trichlorophenol | TCP |
| methylene bisthiocyanate | MBT |

EXAMPLE 1 (Wettable Powder)

A wettable powder was prepared by homogeneously mixing together 3% TBZ, 7% DOIT, 5% polyoxyethylene octylphenyl ether sulfate and 85% clay, followed by pulverization.

EXAMPLE 2 (Flowable Formulation)

A flowable formulation (suspension) was prepared by mixing together 5% BICM, 5% CMIT, 2.5% polyoxyethylene nonylphenyl ether, 2% dioctyl sulfosuccinate, 1.5% white carbon, 0.2% xanthan gum and 83.8% water, followed by passing through a wet grinder.

EXAMPLE 3 (Flowable Formulation)

A flowable formulation (suspension) was prepared by mixing together 4% BICE, 6% CMIT, 2.0% polyoxyethylene stylylphenyl ether, 1% dioctyl sulfosuccinate, 1.5% white carbon, 0.2% xanthan gum and 85.3% water, followed by passing through a wet grinder.

CONTROL EXAMPLES

There were prepared corresponding formulations same as those of EXAMPLES 1, 2 and 3 except that the content of the active ingredient was 10% each of BICM, BICE, TBZ, CMIT, and DOIT above. Further, similar formulations containing 5% of one of the compounds of the general formula (I) or (II) in combination with 5% of MBT or TCP were prepared. These formulations were used as control examples.

TEST EXAMPLE 1 (Fungus Resistance of Emulsion Paint)

A vinyl acetate-acrylic type emulsion paint (ENVI ® #60, a product of Shinto Paint Company, Limited) added with a specified amount of the antifungal agent was uniformly coated on qualitative test filter paper in an amount (weight) same as that of said filter paper and then dried to prepare a specimen. Thereafter, antifungal effect was evaluated in accordance with the test method of paint as described in "Methods of Test for Fungus Resistance" stipulated in JIS Z 2911. In the test conducted, there were used as the test strains Penicillium sp. and Cladosporium sp. which had actually grown on the surface of the specimen in addition to the strains specified in the aforesaid JIS Z 2911. The results obtained are shown in Table 1. In the Table, the degree of fungus growth was determined according to the following ratings.

| | |
|---|---|
| (−) | No fungus growth is observed at all on the specimen. |
| (+) | The area of the specimen on which fungus have grown does not exceed 1/10 of the total area of said specimen. |
| (++) | The area of the specimen on which fungus have grown is 1/10 to ⅓ of the total area of said specimen. |
| (+++) | The area of the specimen on which fungus have grown exceeds ⅓ of the total area of said specimen. |

In the test results obtained in Test Examples 2 and 3, respectively, the same ratings as above were adopted, as well.

TABLE 1

| Composition tested | Amount added (%) | Degree of fungus growth |
|---|---|---|
| No active ingredient contained | 0 | +++ |
| Composition of Example 1 (TBZ 3%, DOIT 7%) | 0.25 | + |
| | 0.5 | − |
| | 1.0 | − |
| | 2.0 | − |
| Control Example (TBZ 10%) (wettable powder) | 0.25 | +++ |
| | 0.5 | +++ |
| | 1.0 | ++ |
| | 2.0 | + |
| Control Example (DOIT 10%) (wettable powder) | 0.25 | ++ |
| | 0.5 | ++ |
| | 1.0 | + |
| | 2.0 | − |
| Control Example (TBZ 5%, MBT 5%) | 0.25 | +++ |
| | 0.5 | ++ |
| | 1.0 | + |
| | 2.0 | − |
| Control Example (TBZ 5%, TCP 5%) | 0.25 | +++ |
| | 0.5 | ++ |
| | 1.0 | + |
| | 2.0 | + |
| Control Example (DOIT 5%, MBT 5%) | 0.25 | ++ |
| | 0.5 | + |
| | 1.0 | + |
| | 2.0 | − |
| Control Example (DOIT 5%, TCP 5%) | 0.25 | +++ |
| | 0.5 | ++ |
| | 1.0 | + |
| | 2.0 | − |

As is clear from the results shown in Table 1, a marked antifungal effect was observed in case of the present composition in comparison with the cases where each of the active ingredients was used alone or in combination with an antifungal compound other than those of the present invention.

TEST EXAMPLE 2 (Fungus Resistance of Wood)

A sapwood of Scotch pine (2 cm width ×5 cm length ×0.5 cm thick) was dipped for 30 seconds in a bath containing the active ingredient diluted to a specified concentration, followed by air drying. This specimen was placed on a potato dextrose agar plate, and 1 ml of a mixed fungus spore aqueous suspension was sprayed over the specimen, followed by culturing at 28° C. for 14 days. The test strains used were Chaetominum globosum, Tricoderma viride, Penicillium funiculosum and a wild strain (Fusarium sp.) actually grown on the Scotch pine. The results obtained are shown in Table 2.

TABLE 2

| Composition tested | Concentration of bath (%) | Degree of fungus growth |
|---|---|---|
| No active ingredient contained | 0 | +++ |
| Composition of Example 2 (BICM 5%, CMIT 5%) | 0.5 | + |
| | 1.0 | − |
| | 2.0 | − |
| | 4.0 | − |
| Control Example (BICM 10%) (suspension) | 0.5 | ++ |
| | 1.0 | ++ |
| | 2.0 | ++ |
| | 4.0 | + |
| Control Example (CMIT 10%) (suspension) | 0.5 | +++ |
| | 1.0 | + |
| | 2.0 | + |
| | 4.0 | − |

As is clear from the results shown in Table 2, a marked antifungal effect of the present composition was observed in comparison with the cases where the active ingredients were used singly as shown in Control Examples.

TEST EXAMPLE 3 (Fungus Resistance of Sized Cotton Cloth)

A mixture comprising 5 parts wheat starch, 2.5 parts PVA, 0.5 part Maconol® H (a softener, a product of Matsumoto Fats & Oils Co. Ltd.) and 92 parts water was heated to prepare a sizing solution. The sizing solution was incorporated with a specified amount of the active ingredient, and thereafter broad cotton cloth was dipped with said sizing solution of the same weight as that of said cotton cloth and then dried. Thereafter, antifungal performance of the active ingredient thus incorporated was evaluated on the basis of the Textile Product Test Method (wet process) as stipulated in "Methods of Test for Fungus Resistance" of JIS Z 2911. In the test, there were used as the test strains Cladosporium sp. and Alternaria sp. actually grown on the cotton cloth in addition to the strains as specified in said JIS Z 2911. The results obtained are shown in Table 3.

TABLE 3

| Composition tested | Amount added (%) | Degree of fungus growth |
|---|---|---|
| No active ingredient contained | 0 | +++ |
| Present composition of Example 3 (BICE 4%, CMIT 6%) | 0.05 | + |
| | 0.1 | + |
| | 0.2 | − |
| | 0.4 | − |
| Control Example (BICE 10%) (suspension) | 0.05 | +++ |
| | 0.1 | +++ |
| | 0.2 | ++ |
| | 0.4 | − |
| Control Example (CMIT 10%) (suspension) | 0.05 | +++ |
| | 0.1 | ++ |
| | 0.2 | + |
| | 0.4 | − |

As is clear from the results shown in Table 3, a marked antifungal effect of the present composition was observed in comparison with the cases where the active ingredients were used singly as shown in Control Examples.

The compositions of the present invention, as can be evidenced by the foregoing test examples, exhibit a markedly improved effectiveness in comparison with the cases where the compositions used contain the active ingredients alone, or in combination with an antifungal compound other than those contemplated herein, and that they are quite suitable as antifungal agents for use in various industrial material and products.

What is claimed is:

1. An industrial antifungal composition which comprises a synergistic mixture of 10–90% by weight of methyl 2-benzimidazole carbamate, based on the total weight of effective ingredients, and 4,5-dichloro-2-octylisothiazoline-3-one.

* * * * *